United States Patent
Leonard et al.

(10) Patent No.: US 8,911,440 B2
(45) Date of Patent: Dec. 16, 2014

(54) RESORBABLE AND RADIOPAQUE DEVICE FOR BONE FIXATION

(75) Inventors: Alain Leonard, Nosy (MG); Carole Leonard, Paulhac (FR); Cyril Sender, Toulouse (FR); Olivier Lignon, Lavaur (FR); Gautier Halbin, Fontenilles (FR); Nouredine Sahraoui, Toulouse (FR)

(73) Assignee: Teknimed, Vic-en-Bigorre (FR)

( * ) Notice: Subject to any disclaimer, the term of this patent is extended or adjusted under 35 U.S.C. 154(b) by 159 days.

(21) Appl. No.: 13/603,544

(22) Filed: Sep. 5, 2012

(65) Prior Publication Data

US 2014/0039562 A1    Feb. 6, 2014

(30) Foreign Application Priority Data

Aug. 2, 2012    (FR) ..................... 12 57514

(51) Int. Cl.
  *A61B 17/56*  (2006.01)
  *A61B 17/58*  (2006.01)
  *A61F 2/30*  (2006.01)

(52) U.S. Cl.
  USPC ........................................... 606/77; 606/286

(58) Field of Classification Search
  USPC ....................................... 606/76–77
  See application file for complete search history.

(56) References Cited

U.S. PATENT DOCUMENTS

| 2006/0121084 A1 | 6/2006 | Borden et al. |
| 2008/0177330 A1* | 7/2008 | Ralph et al. ................... 606/290 |
| 2010/0316591 A1 | 12/2010 | Cotton et al. |

FOREIGN PATENT DOCUMENTS

| WO | 03059409 A2 | 7/2003 |
| WO | 2005009496 A1 | 2/2005 |
| WO | 2007140325 A2 | 12/2007 |

OTHER PUBLICATIONS

French Search Report, dated Apr. 15, 2013, from corresponding FR application.

* cited by examiner

*Primary Examiner* — Andrew Yang
(74) *Attorney, Agent, or Firm* — Young & Thompson

(57) ABSTRACT

An osteosynthesis device that is both resorbable and radiopaque, produced using gradually degrading materials, includes at least one plate and a set of screws made of resorbable material, in which the plate consists of a composite mixture including i) a resorbable polymer or copolymer compound and ii) an inorganic filler that consists of at least one resorbable ceramic. The screws can be made of resorbable polymer, or of a composite mixture with at least one resorbable ceramic. The device is totally resorbable and radiopaque, and it offers a high level of safety, ensuring a strong and durable fixation of the screws to the plate and in the bone during the entire period needed for bone uniting.

14 Claims, 2 Drawing Sheets

RESORBABLE AND RADIOPAQUE DEVICE FOR BONE FIXATION

This invention belongs to the field of surgical equipment and, more specifically, relates to fixation systems used in bone repair.

Its object is an osteosynthesis device that is both resorbable and radiopaque, made using a composite mixture of materials that gradually degrade comprising at least one polymer or copolymer compound and an inorganic filler provided by a ceramic.

Osteosynthesis combines all of the procedures that make it possible to hold two bone structures in place following a fracture, an arthrodesis, or an osteotomy. This is used, for example, when the reduction (i.e., the putting back of the bone ends opposite each other) cannot be done by external maneuvers or when the two fragments are not stable. Osteosynthesis uses various materials that make it possible to keep between them the two bone fragments (or a bone and an implant): plates, rods, nails, screws, pins, clips, etc. The purpose is to achieve uniting of the bone in anatomical position.

Osteosynthesis by plate and screw has been used in bone surgery for tens of years. The plates can be of various shapes (straight, long, curved, X-shaped, etc. . . . ) depending on their placement, and are held by screws of different diameters and different lengths. These materials are made with materials tolerated by the body, especially since they are not always removed after uniting of the bone.

Osteosynthesis by plate and screw is considered a reliable means to attain good bone uniting, when this can be completely achieved. To do this, a certain number of conditions must be met, or at least sought. To begin with, it is vital to ensure rigid holding. The thickness of the plate must be calculated to withstand the stresses applied to the segment in question, based on the strength capacities of the material that constitutes the plate used. For example, in the case of a fracture of the humerus, fixation will be done by a thick metallic plate (for example 3 mm). A second condition is that the plate must be firmly attached to the bone, the screws must remain in place despite vibrations or other stresses that can create play and lead to their loosening. In the above-mentioned example, the plate will be attached to the bone with three to four bicortical screws on both sides of the focal point of the fracture, because the stresses to which the humerus is subjected are considerable. Of course, the characteristics of the screws (shape, size) are selected in relation to those of the plate with which they work.

The material used will also play an important role. The plate and screw devices offered to surgeons have for a long time been made of metal, generally titanium or stainless steel. These metals or metal alloys, although perfectly tolerated by the body, present two drawbacks. On the one hand, since the plate is only rarely removed (approximately 15% of cases), it will be involved over time in the kinematic functioning of the organ that it has allowed to mend. Now, the fact that it remains in place means that the mechanical stresses are not uniformly transmitted in the bone in question. This results in a weakening of the bone at the points of contact between the bone and the plate, namely, essentially at the screws. Secondary fractures are thus frequent.

The use of systems made of synthesis polymers offers an improvement from this point of view because of their greater elasticity. However, on the other hand, these polymers have a weaker mechanical strength than that of the metals, but also than that of the bones. Their lower resistance to bending requires a greater thickness to obtain the same level of rigidity as that of metallic parts. The plate and screw systems are thus most often oversized compared with their metallic equivalent. For example, a metal plate for the wrist commonly has a thickness of approximately 1 mm, whereas to obtain an equivalent strength in the same indication, a plate made of resorbable polymer will need to have a thickness of at least 3 mm.

In both cases, the plate has a significant thickness which, although it is reduced as much as possible with the metallic systems, in the medium- and long-term, leads to risks of irritating nerves and/or tendons that pass nearby. This can also lead, over time, to a severing of said nerves or tendons.

To eliminate these drawbacks, an alternative has been proposed that is based on the use of resorbable materials. Polymers are used that offer the advantage of being totally resorbable over time, i.e., they gradually disappear from the body, after a lapse of time, which can vary from one particular polymer to another, but which is sufficient for the bone to have regained its strength. For example, polymers are known that belong to the family of PLAs (for polylactic acids, or in French acides polylactiques) and PGAs (for polyglycolic acids, or acides polyglycoliques in French).

However, the use of polymers, whether resorbable or not, presents other difficulties that limit their extensive use in surgery.

A first problem arises from the stability of the assembly. The current, better-performing metal screw and plate systems are locking systems. In this case, the screw has a first thread on the shank that functions during penetration and to keep the screw in the bone; and it has a second thread, finer than the first, located at the head of the screw, which takes hold in the plate at the end of travel to lock the screw in its stop position. Now, the polymer plate-screw systems are not suitable for this type of fixation, on the one hand, because plastics technology techniques do not make it possible to mass-produce parts with such a fine feature and, on the other hand, because the relatively weak strength of the material would not be sufficient. This is a significant disadvantage of polymers (in particularly resorbable polymers) faced with the metal.

Secondly, one problem, and by no means the least, arises from post-operative follow-up, because the polymers are totally radio-transparent. Even if this can be an advantage in certain cases (MRI for example), in general, the fact of not being able to visualize the position of the implanted device represents a major drawback. Actually, the radiographs for monitoring will show neither the plate nor the screws, so that the surgeon is unable to know exactly where the materials that he just put in place are located, nor verify over time the state of fixation and change in regard to the bone. This monitoring, however, is essential for the long-term safety of the patient.

When there is recourse to resorbable polymers, the fact that the surgeon cannot verify the progress of resorption of the implanted system adds to the previously mentioned drawbacks. Now, it can happen that the screws degrade more quickly than the plate. This can result in a migration of the plate outside of its implantation area and cause inflammation. Monitoring is thus equally vital when a resorbable plate and screw system is used.

The confidence of the surgeon in resorbable polymer devices has therefore not been gained, whereas the gradual disappearance of the implanted material represents a considerable advantage for the patient, both during the phase of uniting the bone and, in the long term, after its healing.

The object of this invention is to propose a resorbable plate-screw system that makes it possible to overcome the problems that have just been set forth, by reconciling the various identified stresses and without losing the advantages already established by the existing systems. In particular, it is desired to benefit from the resorbable nature, while offering a high level of safety, ensuring a strong and durable fixation of the screws to the plate and in the bone for the entire period needed for uniting of the bone. One objective is thus to be able to achieve a locking of the screws in the plate. Another objective is to make it possible to monitor the position of the plate and the screws in the course of their degradation. In addition, it is desired to attain improved mechanical properties, closer to those of the bone structures, in particular, in regard to the elastic nature. To do this, a plate and screw device made of totally resorbable materials, that is at least partially radiopaque and whose mechanical strength is improved, has been developed.

More specifically, the bone fixation device, according to the invention, comprises at least one plate and a set of screws made of resorbable materials, said plate consisting of a composite mixture that comprises i) a resorbable polymer or copolymer compound and ii) an inorganic filler that consists of at least one resorbable ceramic.

Composite mixture is defined, by its similarity with the expression used in dentistry, as a material comprising inorganic fillers embedded in an organic (or synthetic) matrix. In a unique manner, it has been found that different kinds of resorbable materials, one being organic, the other inorganic, can be combined to obtain an osteosynthesis material that is both totally resorbable and radiopaque, while presenting completely satisfactory mechanical characteristics, even better than certain systems currently used.

The resorbable nature of a material is defined in surgery as the property that it has of gradually degrading in the body. In this case, the polymers degrade while releasing water and carbon dioxide that the body is able to eliminate without any negative effect. As for the ceramics, they release calcium, phosphate, and other ions in smaller quantities, which, for the most part, are integrated into the neighboring bone. Also, sometimes the terms bioresorbable or biodegradable are encountered to signify that the degradation takes place in a biological environment. The degradation speeds are variable as a function of the size of the object and the material itself. One skilled in the art knows numerous materials used in therapeutic applications, that gradually disappear on contact with the water in the body within more or less long time intervals, compatible, in particular, with bone uniting, and that he describes as resorbable.

The resorbable ceramics are currently and routinely used in surgery as a material for filling-in bones. They are provided in different forms (pastes, gels, powder, or in solid cube, rod or wedge shapes) to plug gaps and strengthen by forming a porous structure that the bone cells will colonize. They reinforce the bone while serving as a support for new cells that replace them as they degrade, while releasing ions that participate in return in bone remodeling. This type of material is very brittle and fragile, and is not used for making structural implants.

The composite mixture defined here has proven to impart to the bone fixation device different mechanical properties than those of known resorbable devices. This is demonstrated, first of all, by the fact that the materials used in this invention exhibit a higher Young's modulus than the plates made entirely of polymers, the Young's modulus increasing with the resorbable ceramic filler. By so doing, the elastic deformation capacity has decreased, i.e., the material is more rigid than the polymers by themselves. The modulus of elasticity, without being comparable to that of the metals, is two to three times greater than that of polymer parts, which brings it closer to the inherent characteristics of bones. It is, moreover, more ductile, which means that it can undergo a certain deformation without breaking. This has a certain advantage for the solidity of the screws.

For this reason, the screws designed to keep the plate on the bone ends to be joined can also consist of a composite mixture, identical to or different from that of the plate. They can nevertheless be made simply of synthetic material, although in this case, only the plate that they hold will be visible by radiography techniques. Thus, according to a preferred characteristic of the device that is the object of this invention, the screws consist of at least one resorbable polymer or copolymer compound, alone or in a composite mixture with an inorganic filler that consists of at least one resorbable ceramic.

The organic matrix can consist of at least one simple polymer (formed from a single type of monomer), or else of at least one copolymer (formed from two, or even more, types of monomers). Such compounds, designated together below as "polymeric compounds," which are commonly used to make the osteosynthesis plates and screws, are known. They are essentially polylactic and polyglycolic acids and their copolymers.

Thus, according to the invention, said polymer compound can be advantageously selected from among the polylactic acids (PLA or polylactides), polydioxanones (PDO), polytrimethylene carbonates (PTMC), polyglycolic acids (PGA or polygycolides), polycaprolactones.

Likewise, if the compound i) is a copolymer, the latter can be made of at least two monomers selected from among the enantiopure or racemic lactic acids, dioxanone, trimethylene carbonate, glycolide, caprolactone.

The material chosen for the organic matrix can also be obtained by a physical combination of two or even several polymers or copolymers. In this case, the selected polymeric compounds are mixed and form a uniform mass. Thus, according to a particular embodiment of the invention, the resorbable material that constitutes the plate and the screws can comprise two different resorbable polymer or copolymer compounds.

As already indicated above, the bone fixation device (or at least the plate) contains an inorganic filler, which will also be resorbable and which will impart its radiopacity to it. In a preferred manner, at least one resorbable ceramic is selected from among the calcium phosphates, the calcium sulfates, the strontium phosphates and the strontium sulfates, or any other resorbable inorganic filler known to one skilled in the art. These ceramics are known for their biocompatiblity. They are incorporated into the polymer matrix in powder form.

The inorganic filler can be modified, in quantity and type, to respond to the specifications for the particular devices at each bone segment for which it is designed. This possibility of modification can be taken advantage of in a particularly advantageous manner to improve the solidity of the fixation, by choosing different compositions for the plate and for the screws, so that the respective Young's moduli are different. Actually, a difference in modulus between the material of the plate and that of the screw will make it possible to achieve a better gripping of the screw in the plate. The screw is forced into the plate and can be considered locked like the metallic locking plate-screw systems. A difference of 10 points and more in inorganic filler between screw and plate provides a correct locking with a differential of at least 0.5 GPa between the respective Young's moduli of the screws and of the plate. A difference of more than 20 points is preferred, with, in this case, a differential on the order of at least 1 GPa. However, a 50-point difference will not be exceeded, the part containing the highest ratio of ceramic becoming too rigid and fragile beyond this value.

Thus, according to an advantageous characteristic of the device that is the object of the invention, the ceramic content of the plate is greater by at least 10 points, and preferably by at least 20 points, than the ceramic content of the screws, not to exceed 50 points.

In an advantageous manner, according to the invention, the plate is composed of 10% to 50% ceramic. Preferably, it can be composed of 25% to 35% ceramic by weight, relative to the total weight of the composite mixture. These proportions are selected as being those for which the different mechanical characteristics are optimally combined, in particular the rigidity/ductility ratio, to respond to the objectives of this invention. One skilled in the art will know how to adjust them according to specific needs, as a function of the chemical nature of the polymeric compound and the specifications of the ceramic powder.

By so doing, the screws can contain 0% to 30% ceramic. Preferably, the ceramic content of the screws can be fixed at a level ranging from 5% to 15% by weight relative to the total weight of the composite mixture. There is thus a composite mixture less rich in inorganic filler: the small size of these parts, which would break if a ceramic ratio identical to that of the plate was used, is taken into account. Such a composition also imparts to the screws better torsional strength to tolerate screwing in without damage.

Two additional major advantages are based on this ceramic content made smaller in relation to that of the plate. The first is that the difference in the modulus of elasticity that results from this ensures an improved gripping of the screw in the plate, thus achieving an effective locking.

The second advantage is that the speed of degradation of the part is greater more particularly as the polymer content of the composite mixture is reduced.

This opens up the possibility of monitoring of the resorption speed by a modulation of inorganic filler and organic matrix ratios in the different parts of the device that is the object of the invention. First, the components can be selected that make it possible to obtain a degradation according to a determined and selected rate. Second, and in a particularly advantageous manner, the resorption speed of the different parts (screws and plate) can be differentiated. During the degradation of a plate-screw system, degradation of the screws more quickly than the plate and migration of the plate in a totally undesirable manner outside of the implantation site will thus be avoided.

According to the invention, this type of problem can be remedied by selecting the compositions so that the composite mixture of the plate degrades more quickly than that of the screws. The ceramic content can be an adjustment factor for this purpose, the composite degrading all the more quickly since it contains ceramic. Another parameter can be conveniently used, namely the choice of the ceramic itself.

For example, since β-tricalcic phosphate has a degradation speed greater than that of calcium-strontium hydroxyapatite, the former will be used advantageously in the plate, and the latter in the screws. In this way, the plate will degrade more quickly than the screws, thus eliminating the risks of plate migration outside of the implantation site. According to a particularly advantageous embodiment, in the device, according to the invention, in addition to the polymer or copolymer compound, the inorganic filler of said plate is composed of β-tricalcic phosphate, and the inorganic filler of said screws is composed of calcium-strontium hydroxyapatite.

Lastly, carefully choosing the composition of the polymer is recommended, because it is extremely important on several levels. Actually, whereas a metallic plate is inert and brings no new component into the human body, a resorbable plate will, on the contrary, release monomers and oligomers. It can also fracture into small pieces causing secondary inflammatory reactions. All of this contributes to limiting the confidence of the surgeons.

For this reason, according to a preferred characteristic, the plate and the screws are composed of a composite mixture including a 70:30 poly(L-lactide-co-D,L-lactide) and a ceramic inorganic filler. These copolymers are thermoplastic aliphatic polyesters obtained from the enantiopure L-isomer and from the racemic form of lactic acid in a 70-to-30 ratio by mass, which have mechanical properties close to those of 100 poly(L-lactide), and which, unlike the latter, exhibit the advantage of remaining in the amorphous state throughout the degradation process. Because of this, they degrade layer by layer from the outside to the inside, releasing lactic and glycolic acids as well as oligomers that can be absorbed by the body, without generating small particles that can give rise to secondary inflammatory reactions.

This invention will be better understood thanks to the description that will be given of certain variant embodiments, in connection with the attached figures, in which.

EXAMPLE 1

Radius Plate with Transparent Screws

Figure 1:
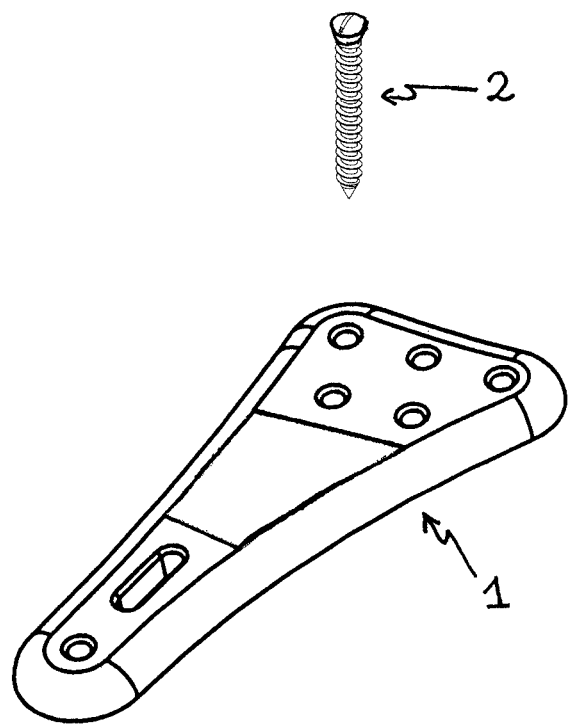
FIG. 1 is a perspective view of an osteosynthesis device including a radius plate and one of its screws.

An anterior radius plate composed of a composite mixture consisting of 70% poly(70/30; L/DL) lactide and 30% β-tricalcic phosphate was produced. The copolymer was obtained from EVONIK (RESOMER LR). The ceramic used is β-tricalcic phosphate manufactured by TEKNIMED. The matrix and the ceramic were chemically mixed. The powder obtained was used by injection molding. The plate 1 obtained is represented in FIG. 1.

A set of resorbable but non-opaque screws 2 made of poly(70/30; L/DL)lactide (RESOMER LR supplied by EVONIK) was shaped by injection molding. One of these screws 2 is represented in FIG. 1.

The Young's moduli of the two materials were determined to be 5.4 GPa for the composite mixture of the plate compared with 3.2 GPa for the polymer material of the screws, or a differential of 2.2 GPa. Simulations on synthetic bone models have been carried out that have demonstrated that the locking is excellent. The mode of rupture is actually the breaking of the plate and not the unlocking of the screws.

The device was tested by implantation on the radius of nine sheep and its evolution was observed for 1 year. The plate shows a perfect biointegration (ability of a material to be colonized by living cells) at 3 months, 6 months, and 1 year on all of the animals. Also, after one year of implantation, it is found that the plates are considerably more degraded than the screws, even in one case, the plate was totally resorbed.

It has also been observed that the screws remained totally solid with the plate in which they are inserted: the locking of the screws on the plates is still ensured after one year.

EXAMPLE 2

Radius Plate with Opaque Screws

An anterior radius plate composed of a composite mixture consisting of 50% poly(70/30; L/DL) lactide and 50% β-tricalcic phosphate was produced. The copolymer was obtained from EVONIK (RESOMER LR). The ceramic used is β-tricalcic phosphate manufactured by TEKNIMED. The matrix and the ceramic were chemically mixed. The powder obtained was used by injection molding, in the same shape as in Example 1 (FIG. 1).

A set of resorbable and opaque screws, composed of a composite mixture consisting of 90% poly(70/30; L/DL)lactide and 10% calcium-strontium hydroxyapatite was produced. The copolymer is supplied by EVONIK (RESOMER LR). The calcium-strontium hydroxyapatite is manufactured by TEKNIMED. The matrix and the ceramic were chemically mixed. The powder obtained was used by injection molding.

EXAMPLE 3

Evolution of the Young's Modulus and of the Elongation

A range of composite mixtures was prepared comprising a copolymer, in this case of poly (70/30; L/DL)lactide, and a ceramic, in this case of TCP (β-tricalcic phosphate), with different contents, according to the same protocol as in Example 1.

Figure 2:
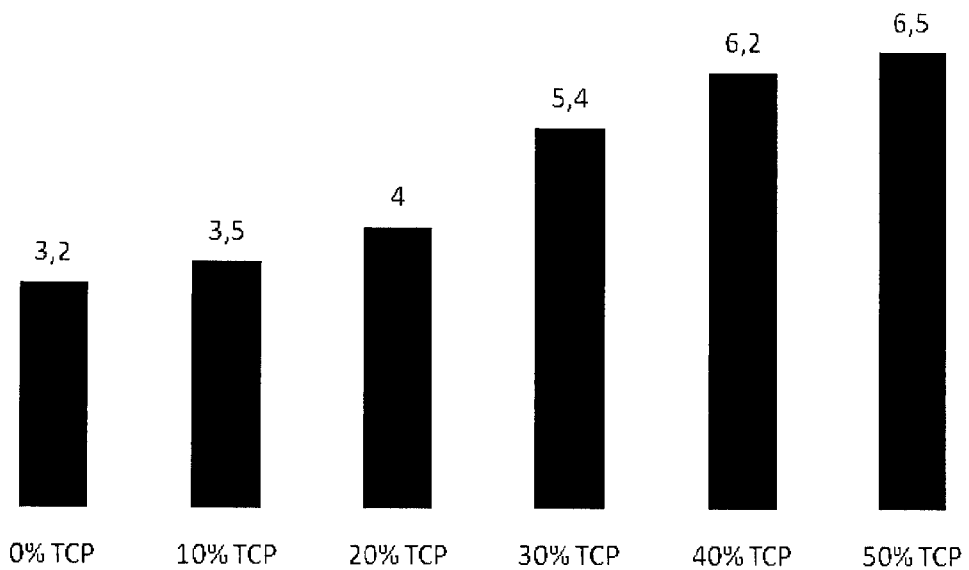
FIG. 2 is a diagram showing the evolution of the Young's Modulus (in GPa) as a function of the inorganic filler of a composite mixture used in the invention.
Figure 3:
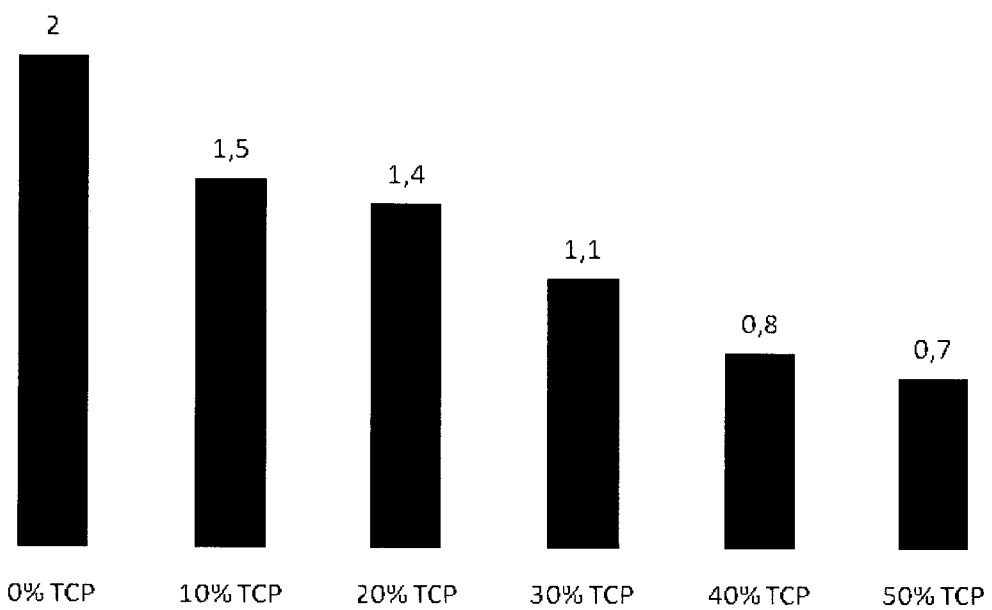
FIG. 3 is a diagram showing the evolution of the maximum elongation before rupture as a function of the inorganic filler of a composite mixture used in the invention.

The diagram shown in FIG. 2 shows the evolution of Young's Modulus (in GPa). The diagram shown in FIG. 3 shows the evolution of the elongation to rupture (in %).

The composite mixture exhibits a higher Young's modulus than the 100% polymer material, and it increases with the resorbable ceramic filler. Conversely, the maximum elongation decreases when the concentration of ceramic increases. The more the concentration of ceramic increases, the more the material becomes hard and brittle.

This demonstrates the advantage of using, according to the invention, a composite mixture that is richer in ceramic for manufacturing a plate, so as to give priority to rigidity, but to use a composite mixture that is relatively less rich in ceramic for manufacturing a screw, for which it is more important to give priority to plasticity.

The invention claimed is:

1. A bone fixation device comprising at least one plate and a set of screws made of resorbable materials,
    wherein the at least one plate is made of a first material comprising a composite mixture comprising i) a resorbable polymer or copolymer compound and ii) an inorganic filler comprising at least one resorbable ceramic,
    wherein the screws in the set of screws are made of a second material comprising at least one resorbable polymer or copolymer compound, and
    wherein the first and second materials have different compositions, each with different respective Young's modulus.

2. The device according to claim 1, wherein the at least one resorbable polymer or copolymer compound of the second material is alone or in a composite mixture with an inorganic filler of at least one resorbable ceramic.

3. The device according to claim 1, wherein said at least one resorbable polymer compound of the first material is selected from among polylactic acids, polydioxanones, polytrimethylene carbonates, polyglycolic acids, and polycaprolactones.

4. The device according to claim 1, wherein said copolymer compound of the at least one plate is made of at least two monomers selected from among enantiopure or racemic lactic acids, trimethylene carbonate, glycolide, dioxanone, and caprolactone.

5. The device according to claim 1, wherein said first material comprises two different resorbable polymer or copolymer compounds.

6. The device according to claim 1, wherein said at least one resorbable ceramic is selected from among calcium phosphates, calcium sulfates, strontium phosphates, and strontium sulfates.

7. The device according to claim 1, wherein the ceramic content by weight of the at least one plate is greater by at least 10 points than the ceramic content by weight of the screws, not to exceed 50 points.

8. The device according to claim 1, wherein the at least one plate comprises 10% to 60% ceramic by weight relative to the total weight of the composite mixture.

9. The device according to claim 1, wherein the screws comprise 0% to 30% ceramic by weight relative to the total weight of the composite mixture.

10. The device according to claim 9, wherein the screws comprise 5% to 15% ceramic by weight relative to the total weight of the composite mixture.

11. The device according to claim 1, wherein the at least one plate comprises 25% to 35% ceramic by weight relative to the total weight of the composite mixture.

12. A bone fixation device comprising at least one plate and a set of screws made of resorbable material,
    wherein the at least one plate comprises a composite mixture comprising i) a resorbable polymer or copolymer compound and ii) an inorganic filler of at least one resorbable ceramic and
    wherein the inorganic filler of said at least one plate is composed of β-tricalcic phosphate, and screws of the set of screws include an inorganic filler composed of calcium-strontium hydroxyapatite.

13. A bone fixation device comprising at least one plate and a set of screws made of resorbable material,
    wherein the at least one plate comprises a composite mixture comprising i) a resorbable polymer or copolymer compound and ii) an inorganic filler of at least one resorbable ceramic, and
    wherein the at least one plate and screws of the set of screws are composed of a composite mixture comprising a 70:30 poly(L-lactide-co-D,L-lactide) and a ceramic inorganic filler.

14. The device according to claim 2, wherein said at least one resorbable polymer compound is selected from among polylactic acids, polydioxanones, polytrimethylene carbonates, polyglycolic acids, and polycaprolactones.

* * * * *